United States Patent
Grange et al.

(10) Patent No.: US 10,195,067 B2
(45) Date of Patent: Feb. 5, 2019

(54) PROPRIOCEPTIVE ORTHOSIS FOR SUPPORTING A JOINT

(71) Applicant: MILLET INNOVATION, Loriol sur Drome (FR)

(72) Inventors: Odile Grange, Allex (FR); Damien Millet, Valence (FR)

(73) Assignee: MILLET INNOVATION, Loriol Sur Drome (FR)

( * ) Notice: Subject to any disclaimer, the term of this patent is extended or adjusted under 35 U.S.C. 154(b) by 503 days.

(21) Appl. No.: 14/889,410

(22) PCT Filed: Apr. 29, 2014

(86) PCT No.: PCT/FR2014/051019
§ 371 (c)(1),
(2) Date: Nov. 5, 2015

(87) PCT Pub. No.: WO2014/184459
PCT Pub. Date: Nov. 20, 2014

(65) Prior Publication Data
US 2016/0081835 A1    Mar. 24, 2016

(30) Foreign Application Priority Data
May 16, 2013  (FR) ..................... 13 54401

(51) Int. Cl.
*A61F 5/01* (2006.01)
*A61F 13/06* (2006.01)

(52) U.S. Cl.
CPC .......... *A61F 5/0104* (2013.01); *A61F 5/0109* (2013.01); *A61F 13/061* (2013.01); *A61F 2005/0176* (2013.01)

(58) Field of Classification Search
CPC .... A61F 5/0104; A61F 5/0109; A61F 13/061; A61F 2005/0176
See application file for complete search history.

(56) References Cited

U.S. PATENT DOCUMENTS

| 4,287,885 A | 9/1981 | Applegate |
| 6,279,160 B1 * | 8/2001 | Chen ............... A41D 13/065 2/24 |

(Continued)

FOREIGN PATENT DOCUMENTS

| DE | 20 2010 015 972 U1 | 2/2011 |
| EP | 0 115 029 A1 | 8/1984 |

(Continued)

OTHER PUBLICATIONS

Translation of FR2607384.*
Jul. 7, 2014 International Search Report issued in International Patent Application No. PCT/FR2014/051019.

*Primary Examiner* — Tarla R Patel
(74) *Attorney, Agent, or Firm* — Oliff PLC (57) ABSTRACT

An extra-light orthosis includes a woven elastic fabric sleeve, shaped to exert compression forces on a member on either side of and on a joint, and a plate fixed onto an inner face of the sleeve to come into direct contact with the skin on the joint, the plate including an elastic fabric layer onto which a layer of polymer gel is adhered, an annular part shaped to surround the top of a joint protruding area, and a tab extending from an outer edge of the annular part, in an axial direction of the sleeve, the plate adhering to the skin such that, under the effect of the compression forces exerted by the sleeve, when the sleeve is longitudinally stretched, the plate remains stretched and applies tensile forces locally to the skin parallel to the surface of the skin, toward the center of the annular part and of the joint.

14 Claims, 6 Drawing Sheets

(56) References Cited

U.S. PATENT DOCUMENTS

2002/0095107 A1\*　7/2002　Martin .................... A61F 13/06
　　　　　　　　　　　　　　　　　　　　602/61
2012/0078156 A1　3/2012　Platz et al.
2013/0060181 A1　3/2013　Fontaine et al.

FOREIGN PATENT DOCUMENTS

FR　　2 607 384 A1　6/1988
FR　　　2607384 A1 \*　6/1988　........... A61F 13/061
FR　　2 772 596 A1　6/1999
FR　　2 957 246 A1　9/2011

\* cited by examiner

PROPRIOCEPTIVE ORTHOSIS FOR SUPPORTING A JOINT

The present invention relates to a proprioceptive orthosis intended to support a joint of the human body. The present invention applies in particular, but not exclusively, to supporting a joint such as the knee or elbow, not requiring any immobilization of the joint. Such an orthosis can be used to prevent chronic pain, or to relieve a slight sprain, or even when resuming work after an injury.

Proprioceptive orthoses for the knee differ from conventional knee supports by adjustments such as "kneecap pelottes" to support the kneecap, or massage pelottes or pads to massage certain muscles. Such orthoses are described for example in the US patent applications 2006/0041214, 2010/0036303 and 2011/0160631, and the model DE 200 05 663 U1. The orthoses described in these documents comprise an annular element made of foam, silicone, silicone rubber or TPU (thermoplastic polyurethane), intended to surround the kneecap and support it.

These orthoses have several defects. They are relatively thick and heavy particularly because they are produced using knitting machines which enable only knitted fabrics to be obtained that cannot be as fine as woven fabrics, i.e. comprising a warp thread and a weft thread. Due to the relatively high weight of the knitted fabric, it may be necessary to provide lateral reinforcements to prevent them from collapsing. Due to their relatively high thickness and to the presence of reinforcements, they are not comfortable under trousers, or even not suitable for wearing under tight-fitting trousers. When the knee is repeatedly bent, when running for example, they tend to slip down the thigh and the leg, particularly due to their weight. In the model DE 20 2010 015 972 U1, non-slip surfaces are provided in the area of the joint and at the ends of the orthosis to avoid such slipping.

When the knee is bent, the folds which inevitably form in the popliteal area, at the back of the knee, are superimposed and may form a thickness of several millimeters, which can cause the user discomfort or even pain. They often require the use of hook-and-loop fastener straps to ensure sufficient hold on the thigh and under the knee.

Furthermore, one well-known method also involves using polymer gel-based plates such as silicone gel or hydrogel-based plates for skin protection or load distribution. For example, to perform a load distribution function, one well-known method involves using a plate made of a relatively hard silicone gel such as PDMS (polydimethylsiloxane). The patent FR 2 712 487 describes a silicone gel having properties similar to those of the footpad to prevent hyper pressure pathologies appearing essentially on or under the feet.

It is desirable to produce a thin orthosis capable in particular of relieving joints, while ensuring the orthosis is held in position. It is also desirable to be able to adjust the forces exerted by the orthosis on the skin and on the underlying tissues, in particular near a joint.

Some embodiments relate to an orthosis comprising a sleeve made of a woven elastic fabric, shaped to exert compression forces on a member on either side of and on a joint, and a plate comprising a layer of a viscoelastic polymer gel fixed onto an inner face of the sleeve to come into direct contact with the skin on the joint. According to one embodiment, the plate comprises a layer made of an elastic fabric onto which the layer of polymer gel is adhered, an annular part shaped to surround the top of a protruding area of the joint, and a tab extending from an outer edge of the annular part, in an axial direction of the sleeve, the plate adhering to the skin such that, under the effect of the compression forces exerted by the sleeve, when the sleeve is stretched longitudinally, the plate remains stretched and applies support forces locally to the underlying member part, toward the center of the protruding area of the joint, and return forces along the axis of the member.

According to one embodiment, the plate is only fixed to the sleeve by a proximal sector of the annular part and by a part including a distal sector of the annular part and the tab.

According to one embodiment, the plate is fixed to the sleeve so as to leave outer side edges of the annular part of the plate free.

According to one embodiment, the plate is fixed to the sleeve along an inner edge of the annular part.

According to one embodiment, the orthosis comprises two lateral pads comprising a layer of viscoelastic polymer gel and having the shape of lateral sectors of the plate fixed by assembly lines extending radially in relation to the plate, beneath lateral sectors of the plate, side edges of the pads being left free.

According to one embodiment, the annular part of the plate has an opening coinciding with a first opening formed in the sleeve, the opening being closed by a piece made of a woven elastic fabric less than 0.3 mm thick fixed onto the sleeve and/or onto the plate.

According to one embodiment, the sleeve comprises a second opening in an area diagonally opposite the plate and closed by a piece made of a woven elastic fabric less than 0.3 mm thick.

According to one embodiment, the piece closing the second opening formed in the sleeve is fixed to the sleeve so as to remain taut whatever the bending of the knee.

According to one embodiment, the sleeve comprises along proximal and distal edges, on its face intended to come into contact with the skin, adherent elements to contribute to the hold of the sleeve on the member.

According to one embodiment, the adherent elements are formed on straps, fixed to the proximal and distal edges of the sleeve, the straps being made of an elastic fabric that may be the same as the fabric of the sleeve.

According to one embodiment, the strap of adherent elements fixed to the proximal edge of the sleeve comprises two straps fixed together and of different lengths to adapt to the shape of the member.

According to one embodiment, the sleeve is less than 0.5 mm thick, and the plate is less than 1 mm thick.

Some embodiments also relate to a method for manufacturing an orthosis comprising steps of: forming a sleeve from a woven elastic fabric, capable of exerting compression forces on a member on either side of and on a joint, forming a plate comprising a layer of a viscoelastic polymer gel, a layer made of an elastic fabric adhered onto the layer of polymer gel, an annular part shaped to surround the top of the joint in flexed position, and a tab extending from an outer edge of the annular part, and fixing the plate onto an inner face of the sleeve to come into direct contact with the skin on the joint, the tab being oriented in a distal direction of the sleeve, the plate adhering to the skin such that, under the effect of the compression forces exerted by the sleeve, when the sleeve is stretched longitudinally, the plate remains stretched and applies tensile forces locally to the skin parallel to the surface of the skin, toward the center of the annular part.

According to one embodiment, the plate is fixed to the sleeve by a seam so that lateral parts of the external edges of the annular part are left free.

According to one embodiment, the manufacturing method comprises a step of fixing by assembly lines extending radially in relation to the plate, pads comprising a layer of viscoelastic polymer gel having the shape of lateral sectors of the plate, beneath lateral parts of the annular part of the plate, side edges of the pads being left free.

According to one embodiment, the manufacturing method comprises a step of fixing a piece of woven elastic fabric to close the opening of the annular part of the plate, the piece of fabric being less than 0.3 mm thick.

According to one embodiment, the manufacturing method comprises steps of forming an opening in the sleeve, opposite the plate, and of fixing a piece of woven elastic fabric to close the opening formed in the sleeve, the piece of fabric being less than 0.3 mm thick.

According to one embodiment, the piece closing the second opening formed in the sleeve, is fixed to the sleeve so as to remain taut whatever the bending of the knee.

According to one embodiment, the manufacturing method comprises a step of molding the plate, the mold forming spikes on the face of the tab intended to come into contact with the skin, to increase the adhesion of the tab to the skin.

According to one embodiment, the manufacturing method comprises steps of fixing, along the proximal and distal edges of the sleeve, straps made of elastic fabric, comprising adherent elements to contribute to the hold of the sleeve on the member.

Some examples of embodiments of the present invention will be described below in relation with, but not limited to, the accompanying figures, in which.

Figure 1:
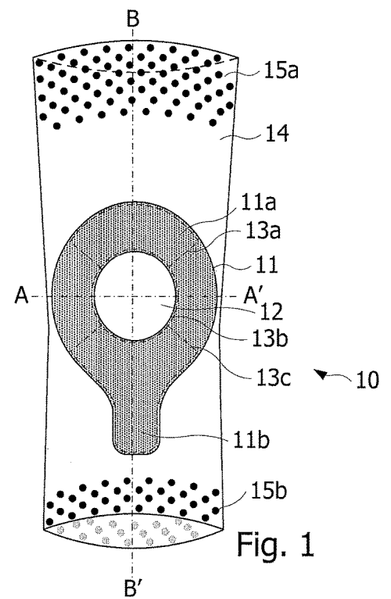
FIG. 1 is a front view of a knee orthosis, according to one embodiment.
Figure 2:
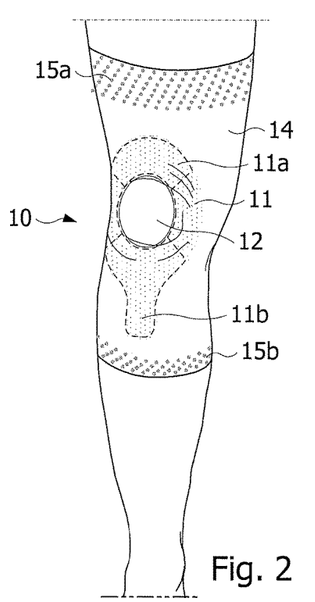
FIG. 2 is a front view of the orthosis in FIG. 1, placed on a right lower limb.

FIGS. 1 and 2 represent a knee orthosis 10 according to one embodiment, FIG. 2 representing the orthosis fitted on a right lower limb. FIG. 1 represents the orthosis in an inside-out configuration, the visible face being the one intended to come into contact with the skin. The orthosis 10 comprises an elastic sleeve 14 and a plate 11 comprising a layer made of a viscoelastic polymer gel, fixed onto the face of the sleeve 14 intended to come into contact with the skin. The sleeve 14 is shaped to exert compression forces on the thigh, the knee and the leg. For this purpose, the sleeve 14 has the shape of a cylinder having a variable diameter in the longitudinal direction of the sleeve, adapted to diameters of the bottom of the thigh, the knee and the top of the leg, so as to obtain desired compression forces in these different parts of the lower limb.

The plate 11 comprises an annular part 11a and a tab 11b extending from an outer edge of the annular part. On FIG. 2, the plate is fixed onto the inner face of the sleeve 14 so that the annular part and the tab come directly into contact with the skin. The plate 11 is fixed at a location of the sleeve 14 so that the annular part 11a can surround the kneecap, and the tab 11b can cover the anterior tibial tuberosity (FIG. 2). The tab 11b thus extends in a distal direction of the sleeve 14. The annular part 11a has an opening 12 having dimensions slightly lower than those of the kneecap and a width between the inner and outer edges (of the annular part) between 2 and 4 cm. The tab 11b has dimensions slightly higher than those of the tibial tuberosity. It shall be noted that in this configuration, it may not be necessary to produce a different orthosis for the right and left knees, despite the fact that the anterior tibial tuberosity is not centered in relation to a longitudinal axis of the thigh passing through the center of the kneecap. The plate 11 on the thigh, the knee and the leg can be less than 0.5 mm thick, for example between 0.35 and 0.45 mm. The sleeve 14 is shaped so as to exert compression forces compliant with standards in force.

Figure 6A:
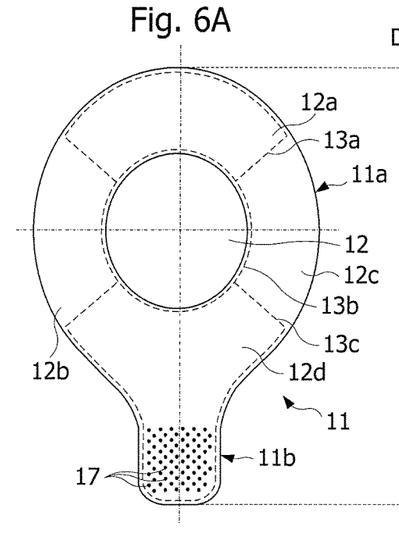
FIGS. 6A, 6B represent a plate of polymer gel of the orthosis in two configurations, respectively depending on whether the knee is stretched or bent.

The plate 11 is fixed onto the sleeve 14 by assembly lines such as seams. In the example of FIGS. 1, 2 and 6A, the plate 11 is fixed by assembly lines 13a, 13b 13c. The assembly line 13a is formed along a proximal part of the outer edge of the annular part 11a over approximately a quarter of the circumference of the annular part. The ends of the assembly line 13a may join the inner edge of the annular part, but this is not essential. The assembly line 13b is formed along the entire inner edge of the annular part 11a. The assembly line 13c is formed along a distal part of the outer edge of the plate 11 including the edge of the tab 11b, over approximately a quarter of the circumference of the annular part 11a. The ends of the assembly line 13c may join the inner edge of the annular part, but this is not essential. In other words, the assembly lines 13a and 13c divide the plate into four sectors 12a to 12d (FIG. 6A) starting from the annular part, i.e. a fixed proximal sector 12a, a fixed distal sector 12d, including the tab 11b, and two lateral sectors 12b, 12c not fixed along the outer edge, each extending over approximately a quarter of the circumference of the annular part 11a. The assembly lines 13a, 13c are produced along all the edges of the proximal sector 12a and the distal sector 12d. The outer edges of the lateral sectors 12b, 12c are thus left free. It shall be noted that the assembly line 13b fixing the inner edge of the annular part 11a to the sleeve is merely used to avoid the formation of any gaping and can thus be totally omitted, or partially by keeping the parts located on the proximal 12a and distal 12d sectors.

Instead of being fixed by assembly lines, the proximal sector 12a and the distal sector 12d of the plate 11 may be fixed onto the sleeve 14 by a layer of adhesive, the lateral sectors 12b, 12c not being adhered onto the sleeve 14.

The sleeve 14 may be made of a woven elastic fabric in two perpendicular directions, along the warp and along the weft of the fabric, for example an elastane polyamide fabric. Therefore, the fabric forming the sleeve may have a maximum stretch (along the fabric weft and warp) ranging between 80 and 110%, for example equal to 95% and a modulus of elasticity equal to 40% ranging between 5 and 7 N, for example equal to 6 N. The fabric forming the sleeve may be less than 0.5 mm thick, for example between 0.3 and 0.45 mm. According to one embodiment, the sleeve 14 may be produced so as to cover the thigh over a length of 18 to 28 cm (to within ±10%) from the axis of the kneecap.

The assembly lines 13a, 13b, 13c may be produced by seams. The assembly line 13b may be formed by overcast.

The plate 11 adheres to the skin such that, under the effect of the compression forces exerted by the sleeve 11, when the sleeve is stretched longitudinally, the plate remains stretched and applies tensile forces locally to the skin parallel to the surface of the skin, toward the center of the annular part. The opening 12 may be closed by a piece of thin woven fabric, which may be fixed onto the orthosis by the assembly line 13b or another assembly line along the inner edge of the annular part 11a.

According to one embodiment, the layer of polymer gel of the plate 11 is formed in a silicone gel obtained by at least partial polymerization of a mixture of silicone oils such as polydimethylsiloxane oils. Such a mixture enables a variety of silicone gels to be obtained that have different properties particularly in terms of hardness and adhesiveness, depending on the respective proportions of the silicone oils forming the mixture, which define the degree of polymerization of the mixture. Thus, by adjusting these proportions, a viscoelastic gel that is more or less hard and adhesive can be obtained. The hardness of the plate can be adjusted by taking account of elasticity and wear resistance requirements given that the plate will be under high mechanical stress.

According to one embodiment, the sleeve 14 comprises along its proximal and distal edges, anchor straps 15a, 15b to hold the sleeve 14 on the thigh and on the leg, to avoid the sleeve 14 slipping along the lower limb, either downwards, or upwards. For this purpose, the anchor straps 15a, 15b comprise elements having a certain adhesion to the skin. The anchor straps 15a, 15b may be made of a fabric which may be the same as the one from which the sleeve 14 is made. The adherent elements of the straps 15a, 15b may have the form of plates, pads or spikes, for example made of polymer gel such as a silicone gel. The surface density of the adherent elements is provided to avoid any inflammation of the skin by friction and shear, which can lead to burns. The adherent elements may be broader along the free edges of the strap 15a and/or 15b, than those formed along the edges of the strap fixed onto the sleeve 14.

The orthosis may be fitted on a lower limb by pulling it on over the foot and by pulling the upper edge of the sleeve 14 until the plate 11 is placed on the kneecap. The natural stiffness of the sleeve fixes the stretch of the sleeve, which is much lower than the elastic limit of the fabric forming the sleeve. It transpires that the stretch of the part of the sleeve covering the thigh, when bending the knee 90°, remains below 20% in the area of the sleeve where the tension is maximum, and remains below 10% at 4 cm from this area toward the strap 15a. This stretch is much lower than the maximum stretch of the fabric forming the sleeve. In these conditions, the alternating bending of the knee when walking or running does not place any great stress on the hold of the sleeve on the thigh, ensured by the strap 15a. As a result, the straps 15a, 15b are sufficient to prevent the orthosis from slipping.

It can be seen that the elastic stresses of the fabric of the sleeve 14 are maximal just above the kneecap and decrease toward the top of the thigh. The sleeve 14 can thus be provided with a sufficient length between the location of the plate 11 and its proximal edge, so as to place the strap 15a in an area of the thigh where the elastic stresses of the sleeve 14 are relatively low (area of low muscle stretch). According to one embodiment, the strap 15a may have a greater width than that of the strap 15b, typically a width twice that of the strap 15b. Thus, the strap 15a may be produced using several narrower straps. The resulting advantage is that it can adapt to the significant variation in diameter of the thigh in this area, by giving the two straps forming the strap 15a different lengths. In the event that the strap 15a is produced using two straps sewn together, one of the two straps may comprise one row of adherent elements less than the other strap forming the strap 15a, to retain an area for sewing the two straps together, without any adherent elements.

Figure 3:
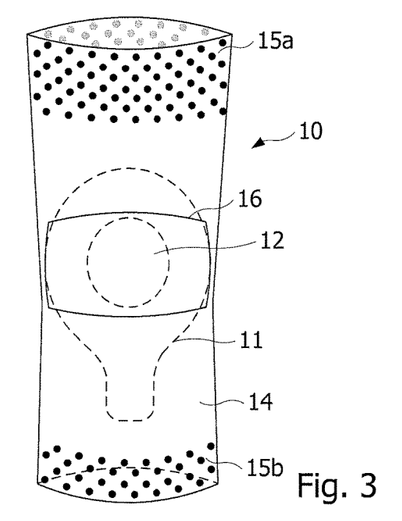
FIG. 3 is a rear view of the orthosis, according to one embodiment.
Figure 4:
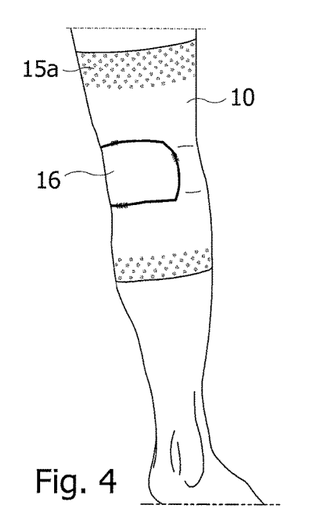
FIG. 4 is a rear view of the orthosis in FIG. 1, placed on a right lower limb.

FIGS. 3 and 4 represent the rear face of the orthosis, according to one embodiment, FIG. 4 representing the orthosis fitted on a right lower limb. The orthosis comprises an opening 16 formed substantially opposite the opening of the plate 11, at a location corresponding to the popliteal area or popliteal fossa of the knee. The opening 16 is closed by a piece of woven fabric that can be fixed onto the sleeve 14 by a seam. The piece of fabric closing the opening 16 may be elastic and be less than 0.3 mm thick. According to one embodiment, the piece of woven fabric closing the opening 16 is made of the same fabric as the one closing the opening 12 of the plate 11. The piece of fabric closing the opening 16 may also be fixed onto the sleeve all around the opening 16 so as to remain taut, whatever the bending of the knee, without introducing any spurious play of forces. In this way, the "invasion" of the popliteus can always be avoided.

Figure 5A:
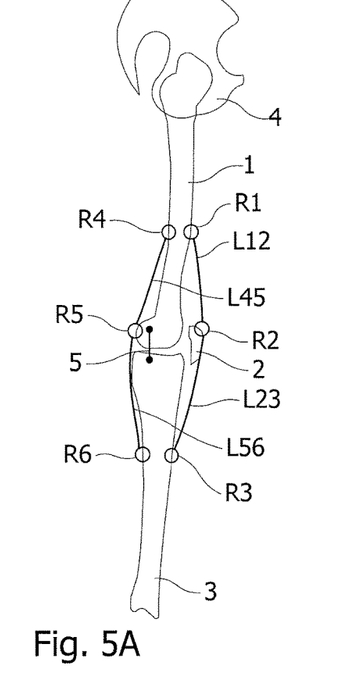
FIGS. 5A, 5B represent in a sagittal section the bones of a right lower limb (iliac bone, femur, kneecap, tibia), respectively with the knee stretched out and bent at 90°.
Figure 5B:
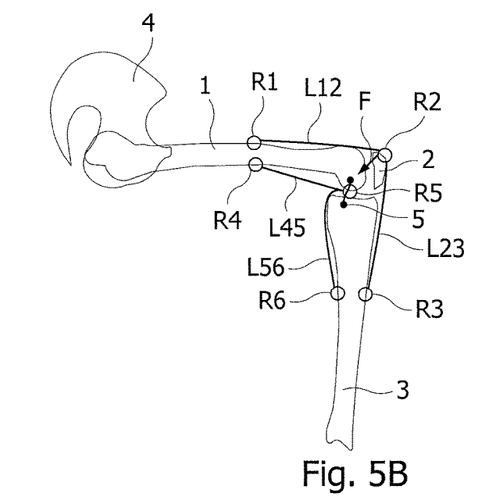
Figure 5C:
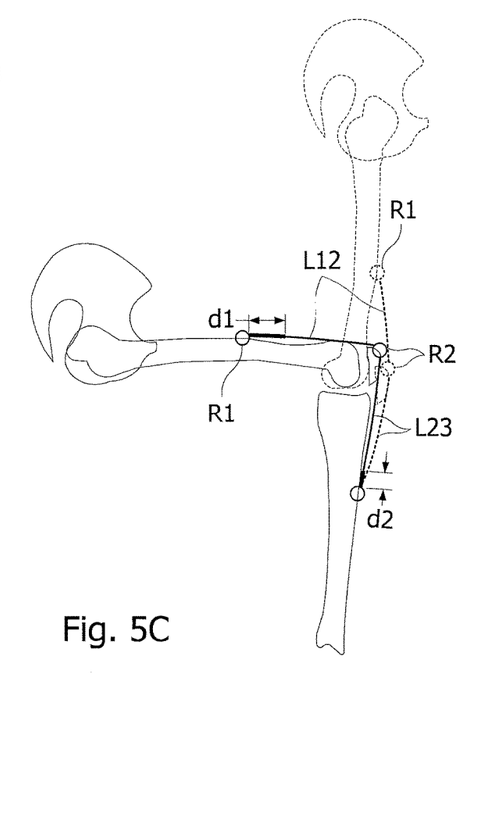
FIG. 5C represents FIGS. 5A and 5B superimposed.

FIGS. 5A, 5B represent the skeleton of a lower limb and of the pelvis in a sagittal section (iliac bone 4, femur 1, tibia 3 and kneecap 2), in configurations of knee stretched and knee bent at approximately 90°. FIG. 5C represents these two configurations, superimposed. FIGS. 5A, 5B symbolize, by circles, anterior R1, R2, R3 and posterior R4, R5, R6 reference points on the bones and, by lines, the tissues (muscles, tendons) L12, L23, L45, L56 linking these reference points. The points R1 and R4 are located at a proximal position of the femur 1. The point R2 is located on the kneecap 2. The point R5 is located at a distal position of the femur 1. The points R3 and R6 are located at a distal position of the tibia 3. These figures show that the anterior links L12 between the points R1 and R2 and L23 between the points R2 and R3 undergo stretches d1 and d2 between the stretched out and bent configurations of the knee (FIG. 5C). However, the link L45 between the points R4 and R5 has the same length in these two configurations. The link R56 between the points R5 and R6 also has the same length in these two configurations, but is distorted in the region of the popliteal fossa in the configuration of knee bent at approximately 90°. Indeed, the functioning of the joint of the knee results, between the femur 1 and the tibia 3, in a rolling and sliding of the femoral condyles over the tibial glenoid cavities and between the femur 1 and the kneecap 2, and by a sliding of the kneecap 2 in the trochlea of the femur 1. A thin elastic fabric 16 is provided on this specific region of the popliteal fossa to avoid the formation of increased thicknesses resulting from a superimposition of folds of fabric, susceptible of causing discomfort or pain when the knee is bent in sitting or squatting position. In excess of one millimeter of thickness, these increased thicknesses can cause irritations, or even burns. Providing the thin fabric 16 is therefore a significant improvement of this type of orthosis.

FIGS. 5A, 5B also represent the internal and external lateral ligaments 5 that are taut when the knee is stretched.

During a bending phase of the knee, the orthosis exerts a force F contributing to supporting the kneecap 2 and to laterally stabilizing the knee.

On FIG. 4, the opening 16 is substantially rectangular, the upper and lower limits being substantially rectilinear. According to one possible embodiment, the upper part may be convex so as to follow the cylindrical shape of the thigh, and thus avoid the appearance of any discomfort for certain anatomies.

The orthosis as described above may have a weight in the order of 50 g (to within ±10%), to be compared with that of the orthoses of the prior art that commonly have a weight greater than 150 g.

Figure 6B:
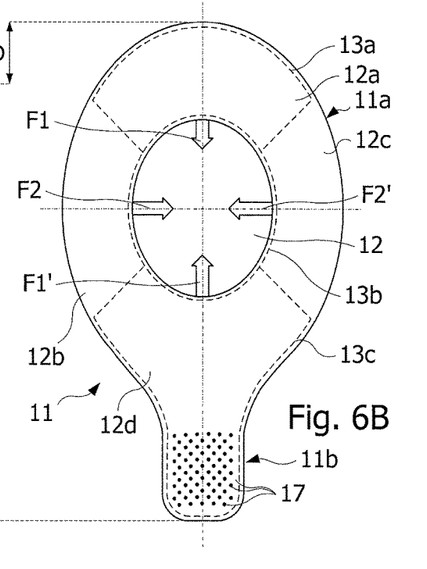

FIGS. 6A, 6B represent the plate 11 in configurations, respectively not stretched and stretched, for example when the orthosis is in place on a lower limb, respectively, knee stretched and knee bent. In non-stretched configuration, the opening 12 of the plate 11 is substantially circular and adapted to the shape of the kneecap. The tab 11b is an anchor point on the skin, obtained by the conjunction of the compression force exerted by the sleeve 14 on the tab 11, of the surface of the tab and in particular of the tab 11b, and of the tack of the polymer gel forming the plate. The strap 15a is an anchor point of the sleeve 14 on the thigh, and the strap 15b is an anchor point of the sleeve on the leg. During the stretching of the sleeve 14, when the knee is bent, a part of the stretches d1, d2 (FIG. 5C) is transmitted to the plate due to its adhesion to the skin, to the anchoring of the sleeve 14 by the straps 15a, 15b, and to an additional anchoring resulting from the link by the annular part 11a of the plate to the kneecap. The result is a stretching D of the plate 11 and in particular of the annular part 11a. The stretching D results in an elastic deformation of the plate 11, causing in particular a deformation of the opening 12 that extends along the longitudinal direction and narrows along the transverse direction. The result is the appearance of tensile forces parallel to the surface of the skin exerted by the plate on the skin and on the volume of the member it surrounds. These forces comprise opposite longitudinal forces F1, F1' oriented toward the center of the opening 12 and opposite transverse forces F2, F2', also oriented toward the center of the opening 12. The forces F2, F2' support the kneecap and avoid its lateral displacement. The forces F1, F1' contribute to the unfolding of the step when walking or running. Therefore, during walking or running, the annular part 11a stretches during an active phase when the foot is placed on the floor whereas the inertia of the body contributes to the bending of the knee. During a passive phase when the foot is no longer resting on the floor and the lower limb stretches forward to take a new step, the annular part 11a recovers its non-stretched configuration and thus transfers to the leg the elastic energy stored. Even though the forces F1, F1', F2, F2' are relatively low, they justify the description of the orthosis as proprioceptive. Indeed, the forces F2, F2' are sufficient to provide the kneecap with a certain support and relieve the joint while offering the feeling that the joint is supported. As for the forces F1 and F1', their presence is felt through the musculotendinous system to which they apply.

Figure 7:
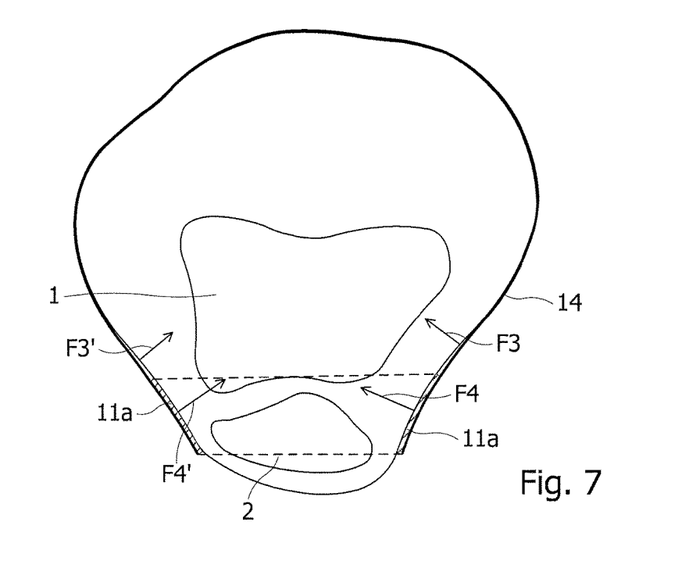
FIG. 7 represents a cross-section of the right knee.

FIG. 7 represents a cross-section of the right knee and of the orthosis surrounding it. It can be seen that the annular part 11a takes a substantially tapered concave form, surrounding the right, left, lower and upper lateral parts of the kneecap 2. FIG. 7 also shows by arrows the forces F3, F3', F4, F4' exerted by the orthosis on the kneecap 2, these forces being exerted perpendicularly to the surface of the sleeve 14 and of the plate 11. The forces F3, F3' exerted by the sleeve 14 are directed toward the center of the knee, and the forces F4, F4' exerted by the annular part 11a of the plate 11 are directed substantially in parallel to the surface of the interface between the kneecap 2 and the femur 1. The orthosis thus ensures the lateral support of the kneecap in particular when the knee is stretched or at the beginning of a bending movement, i.e. in positions where the tissues surrounding it are the least taut.

It shall be noted that the longitudinal extension of the plate 11, in particular of the annular part 11a, is partly made easier by the absence of seams on the outer edge of the lateral sectors 12b, 12c of the annular part 11a. It shall also be noted that the sleeve 14 may have a longitudinal stretching capacity greater than the stretches d1+d2 (FIG. 5C), so as to prevent the proximal and/or distal edges of the sleeve from slipping along the thigh or the leg.

According to one embodiment, the tab 11b comprises spikes 17 to increase its adhesion to the skin (FIGS. 6A, 6B). These spikes may be formed for example when manufacturing the plate 11b by molding.

Figure 8A:
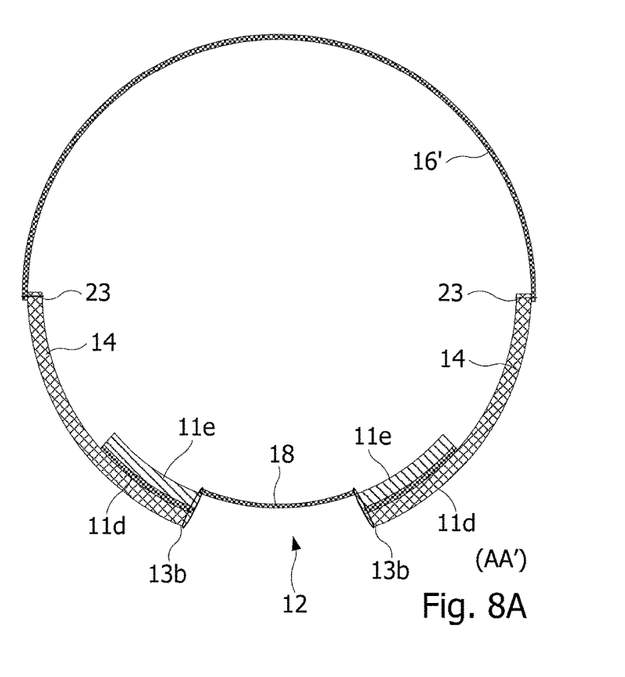
FIGS. 8A, 8B are schematic views of the orthosis in longitudinal and transverse cross-sections, along the planes AA' and BB' indicated on FIG. 1, according to some embodiments.
Figure 8B:
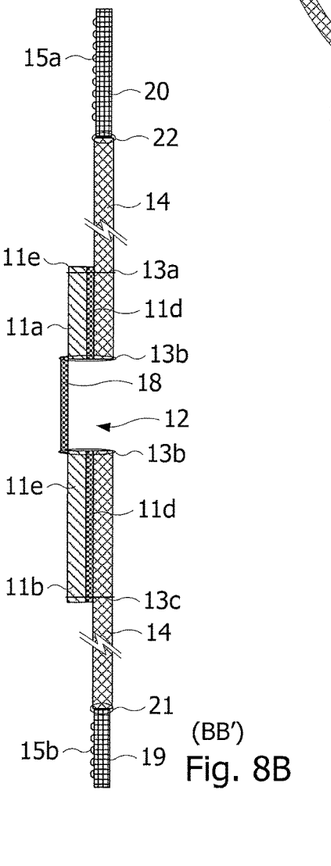

FIGS. 8A, 8B represent the orthosis 10. FIGS. 8A, 8B show in particular the plate 11 comprising the layer of polymer gel 11e adhered onto a piece of woven elastic fabric 11d covering an entire face of the layer of polymer gel, without closing the opening 12 of the annular part 11a. The assembly of the layer of polymer gel 11 e and the piece of fabric 11d forming the plate 11, may then be sewn by the seams 13a, 13b, 13c to the sleeve 14. The seams 13a and 13c can be removed, and replaced by adhering the piece of fabric 11d (adhered onto the layer of polymer gel 11e) to the sleeve 14, by a layer of adhesive spread over the proximal 12a and distal 12d annual sectors (delimited by the seams 13a and 13c). The piece of fabric 11d may be made of the same fabric as the sleeve 14.

The hardness and thickness of the layer of polymer gel 11e of the plate 11 may be chosen so as to be able to sew the entire plate 11 adhered onto the piece of fabric 11d. Furthermore, the tack of the plate 11 can be chosen so as to prevent the latter from slipping on the skin, given the compression forces exerted by the sleeve 14.

Straps 19, 20 anchoring to the skin the proximal and distal edges of the sleeve 14 can be fixed by seams 21, 22 onto the proximal and distal edges of the sleeve 14. The straps 19, 20 have for example plates or pads or spikes 15a, 15b, or even straps, having an adhesion to the skin greater than that of the sleeve 14. An opening 16 corresponding to the rear area of the knee made in the sleeve may be closed by a piece of woven fabric 16' which is for example sewn by a seam 23, for example flat without the sleeve or the piece 16' being previously stretched out. The width of each of the straps 19, 20 and the retaining effect exerted on the thigh or on the leg can be adapted to the desired hold of the sleeve 14 on the lower limb.

According to one embodiment, the sleeve 14 does not comprise any opening opposite the opening 12 of the plate 11.

According to another embodiment shown by FIGS. 8A, 8B, the opening 12 of the annular part 11a is closed by a piece of woven fabric 18 having substantially the same dimensions as the opening 12. The piece 18 can be sewn flat without the sleeve 14 or the piece 18 being previously stretched out. The piece of fabric 18 can be fixed for example on the inner side of the sleeve by the seam 13b or by another seam. The piece of fabric 18 may be elastic, and be less than 0.25 mm thick, for example 0.2 mm thick, and have a maximal stretch ranging between 50 and 90%, for example between 60 and 80%, and a modulus of elasticity at 40% ranging between 1 and 2 N. The piece of fabric 18 may be fixed onto the sleeve 14 so as not to exert any force on its periphery when the sleeve is not taut. When the sleeve 14 is taut, it may be desirable for the piece of fabric 18 not to counter the extension of the plate 11, and to only exert non-significant forces on the kneecap. The piece of fabric 18 has a low modulus of elasticity so as to only prevent the opening 12 from gaping in certain circumstances of use. The seams may be produced so as not to hinder, or to hinder in a limited manner, the stretching of the sleeve along its axis. Therefore, forms of seam such as the looser overcast may be preferred to fix the piece of fabric 18.

It shall be noted that the presence of the piece of fabric 18, if the latter overlaps onto the plate 11, may facilitate the formation of the seam 13*b* or the one that fixes the piece 18. Indeed, the presence of the piece 18 may make it possible to prevent any direct contact between the plate 11 and the sewing machine used to produce this seam, and thus avoid the adhesion of the plate causing the orthosis to be blocked in the sewing machine. It will be understood that other means such as the use of an appropriate lubricant, may be used to avoid such blocking. It shall also be noted that the seam 13*b* may be made in the form of simple stitching that can be removed after fixing the plate 11 onto the sleeve 14.

According to another embodiment shown by FIGS. 8A, 8B, the sleeve 14 comprises the opening 16 opposite the opening 12 of the plate 11. A piece of thin woven fabric 16' may close the opening 16. The piece of fabric 16' may be made of the same fabric as the piece 18.

Figures 9A, 9B, 10:
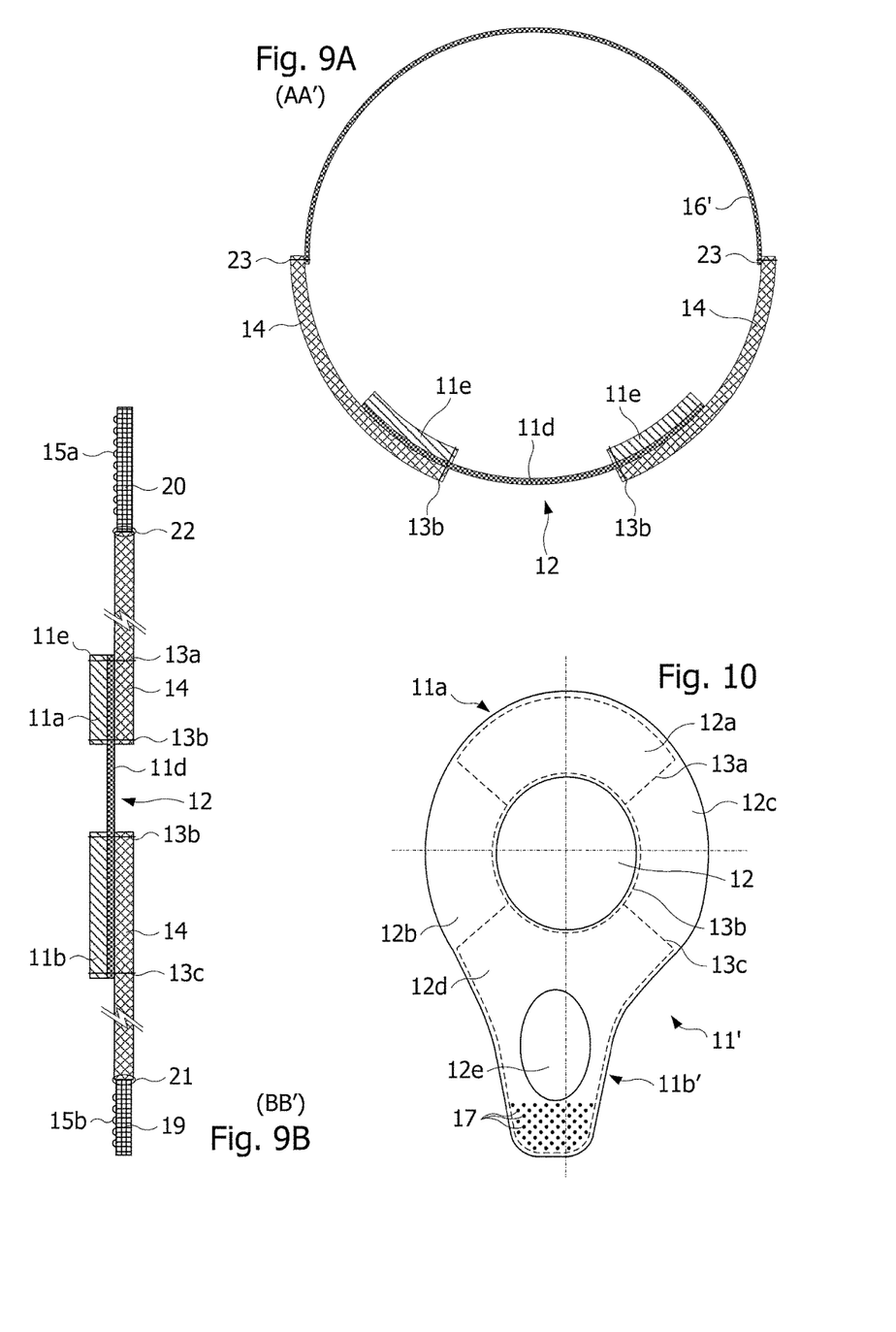
FIGS. 9A, 9B are schematic views of the orthosis in longitudinal and transverse cross-sections, along the planes AA' and BB' indicated on FIG. 1, according to other embodiments.
FIG. 10 represents the plate made of polymer gel according to another embodiment.

FIGS. 9A, 9B represent an orthosis according to another embodiment. The orthosis represented on FIGS. 9A, 9B differs from the one represented on FIGS. 8A, 8B in that the piece of fabric 11*d* onto which the layer of polymer gel 11 e of the plate 11 is fixed is not open opposite the opening 12. The piece of fabric 11*d* thus closes the opening 12. Therefore, it is not necessary to provide the piece 18. As above, the assembly of the plate 11 and of the piece of fabric 11*d* may be carried out by adhesion. The plate 11 (layer of polymer gel 11*e* and piece of fabric 11*d*) may then be fixed onto the sleeve 14 by the seams 13*a*, 13*b*, 13*c* or by a layer of adhesive spread over the proximal 12*a* and distal 12*d* sectors delimited by the seams 13*a*, 13*b*, 13*c*.

Furthermore, as shown on FIG. 9A, the piece of fabric 16' may be fixed onto the inner side of the sleeve 14.

FIG. 10 represents a plate 11' according to another embodiment. The plate 11' differs from the one represented in particular on FIGS. 6A, 6B in that it comprises a tab 11*b*' comprising an opening 12*e* at the location of the anterior tibial tuberosity. As the anterior tibial tuberosity is not located on a longitudinal axis of the thigh passing through the center of the kneecap, the opening 12*e* may be slightly offset. The result is that the orthosis will be different for the right and left knees. As above, the tab 11*b*' may comprise spikes 17 provided to increase the adhesion of the tab on the skin in the presence of the compression forces exerted by the sleeve 14. Provision may also be made to widen the opening 12*c* so as not to have to pair the orthosis.

Figures 11A, 11B, 11C:
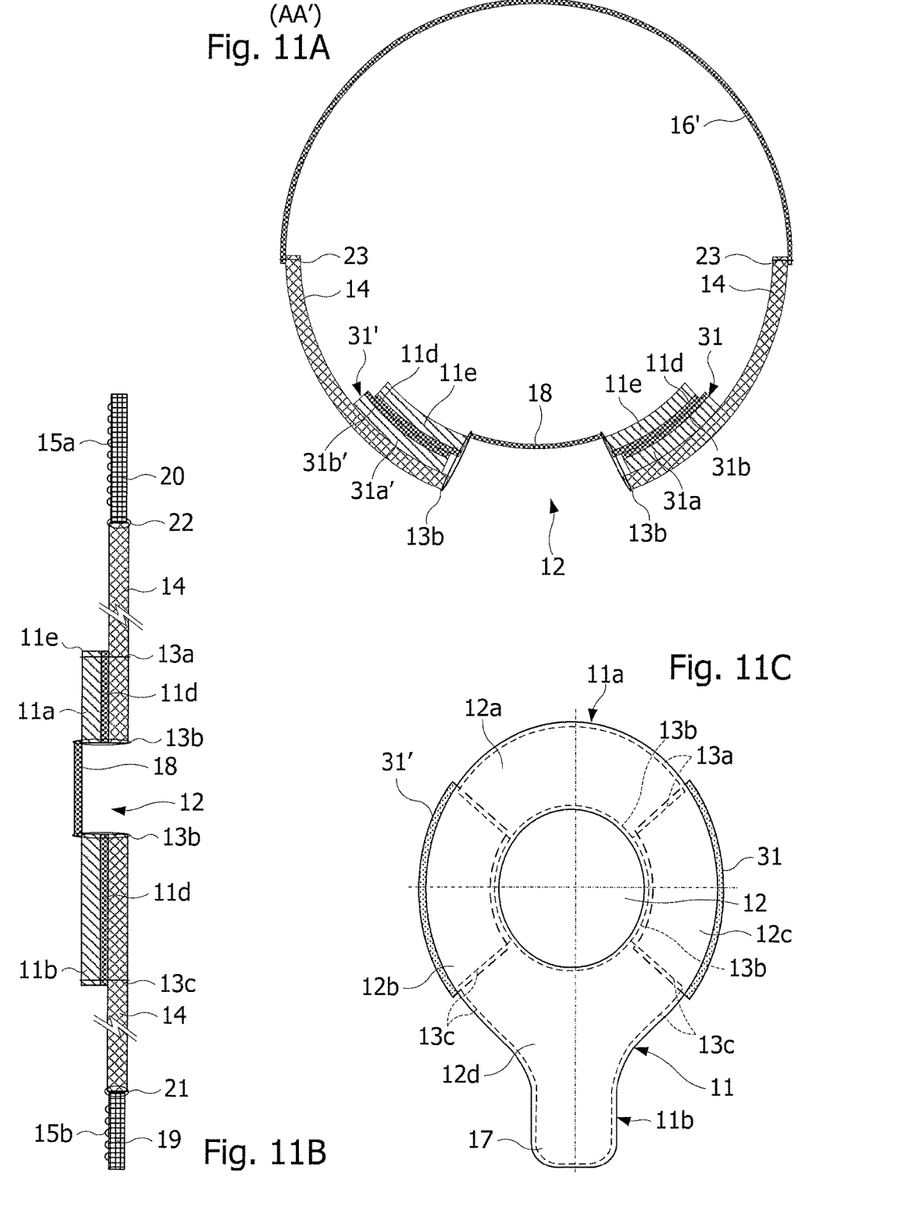
FIGS. 11A, 11B and 11C are schematic views in longitudinal and transverse cross-sections along the planes AA' and BB' indicated on FIG. 1, and of the inner face of the orthosis, according to other embodiments.

FIGS. 11A, 11B and 11C represent an orthosis according to other embodiments. The orthosis represented on FIGS. 11A, 11B and 11C differs from the one represented on FIGS. 8A, 8B in that it comprises in addition to the plate 11, lateral pads 31, 31' comprising a layer of viscoelastic polymer gel 31*a*, 31*a*' adhered onto a layer of elastic woven fabric 31*b*, 31*b*'. The pads 31, 31' have substantially the shape of the lateral annular sectors 12*b*, 12*c* of the plate 11. The pads 31, 31' are fixed beneath the lateral sectors 12*b*, 12*c* of the plate 11, on either side of the opening 12 of the annular part 11*a*. FIG. 11B is identical to FIG. 8B, the pads 31, 31' not being located on the longitudinal axis of the plate 11. The pads 31, 31' are fixed onto the sleeve 14 at their ends by assembly lines extending radially in relation to the plate 11. Thus, the pads 31, 31' may be fixed onto the sleeve 14 at the same time as the plate 11by only the radial parts of the assembly lines 13*a* and 13*c* (and not by the central assembly line 13*b* along the opening 12). Side edges of the pads 31, 31' are thus left free. The pads 31, 31' may laterally slightly exceed the outer edge of the plate 11.

On FIG. 11A, each of the pads 31, 31' comprises a layer of polymer gel 31*a*, 31*a*' previously adhered onto a layer of fabric 31*b*, 31*b*'. The pads 31, 31' are disposed beneath the plate 11 so that the layers of fabric 31*b*, 31*b*' are disposed against the layer of fabric 11*d* of the plate 11. Thus, the layers of polymer gel of the plate 11 and of the pads 31 or 31' are separated by the two layers of fabric 11*d*, and 31*b* or 31*b*'. The pads may be made of the same material as the plate 11 and may have a same thickness as the latter.

It shall be noted that the layers of fabric 31*b*, 31*b*' may be removed, so that the two layers 31*a*, 31*a*' are adhered onto the face of the layer of fabric 11*d* not covered by the layer of polymer gel 11*e*.

On either side of the plate 11, beneath the non-sewn side edges of the latter, provision may be made to form tucks (or gathered seams) in the sleeve 14 to enable the fabric of the sleeve to unfold over the curvature of the knee, despite the increased thickness formed by the double-thickness plate, without applying any excessive compression forces linked to the curvature of the knee to be absorbed.

Providing pads 31, 31' enables the kneecap to be more firmly supported laterally. Indeed, it may be desirable to relieve the ligaments more, in particular when they are under great stress for example when practicing certain sports such as downhill skiing. During this sport, the knees undergo lateral efforts in a more or less bent position, when turning or in order to absorb the unevenness of the ground.

It will be understood by those skilled in the art that the present invention is susceptible of various alternative embodiments and various applications. In particular, the present invention does not apply solely to the joint of the knee, but also to other joints such as the elbow, shoulder, or even the thumb. The shape and the dimensions of the orthosis, in particular of the sleeve and of the plate, are then adapted to the configuration of the joint to be supported. The adaptations thus required to take account of the specific features of the joint that does not necessarily comprise a ball-and-socket joint, are minor and within the understanding of those skilled in the art. However, whatever the joint for which it is intended, the plate comprises an annular part and a tab extending from an edge of the annular part. The opening of the annular part is adapted to the dimensions of a protruding area of the joint to be supported. The tab is provided to be applied onto an area of the skin covering harder tissues than those covered by the annular part of the plate. The shape of the tab may be adapted to the shape of the tissues above which the tab is disposed, to obtain the best possible anchoring. Thus, the tab of the plate may have a length from 4 to 20 cm, and a width from 2 cm to the width of the annular part. For certain joints like shoulders, provision may be made to produce two tabs respectively extending on either side of the annular part.

Furthermore, the support straps 15*a*, 15*b* may be totally or partly removed, by replacing the sleeve with a garment such as capri pants or stretch ski pants (for the knee), covering the pelvis and at least one lower limb of the user that must be supported by the orthosis. The garment may be supported at the ankle by using the tapered shape of the leg in the vicinity of the ankle.

The invention claimed is:

1. An orthosis comprising
   a sleeve made of a woven elastic fabric, shaped to exert compression forces on a member on either side of and on a joint, and
   a plate comprising a layer of a viscoelastic polymer gel, and
   a layer made of an elastic fabric onto which the layer of polymer gel is adhered, wherein:
   the plate is fixed onto an inner face of the sleeve such that the layer of polymer gel comes into direct contact with skin on the joint,
   the layer of polymer gel comprising an annular part shaped to surround the top of a protruding area of the joint, and a tab extending from an outer edge of the annular part, in an axial direction of the sleeve, and
   the layer of polymer gel having an adherence to the skin such that, under the effect of the compression forces exerted by the sleeve, when the sleeve is stretched longitudinally, the layer of polymer gel remains stretched and applies locally to a part of the member to be covered by the layer of polymer gel, support forces towards a center of the annular part, and return forces parallel to the axial direction of the sleeve.

2. The orthosis according to claim 1, wherein the plate is only fixed to the sleeve by a proximal sector of the annular part and by a plate part including a distal sector of the annular part and the tab.

3. The orthosis according to claim 1, wherein the plate is fixed to the sleeve so as to leave outer side edges of the annular part of the plate free.

4. The orthosis according to claim 1, wherein the plate is fixed to the sleeve along an inner edge of the annular part.

5. The orthosis according to claim 1, comprising two lateral pads comprising a layer of viscoelastic polymer gel and having the shape of lateral sectors of the plate fixed by assembly lines extending radially in relation to the plate, beneath lateral sectors of the plate, side edges of the pads being left free.

6. The orthosis according to claim 1, wherein the annular part of the plate has an opening coinciding with a first opening formed in the sleeve, the opening being closed by a first piece made of a woven elastic fabric less than 0.3 mm thick fixed onto the sleeve and/or onto the plate.

7. The orthosis according to claim 1, wherein the sleeve comprises a second opening located in an area diagonally opposite the plate and closed by a second piece made of a woven elastic fabric less than 0.3 mm thick.

8. The orthosis according to claim 7, wherein the second piece is fixed to the sleeve so as to remain taut whatever the bending of the joint.

9. The orthosis according to claim 1, wherein the sleeve comprises along proximal and distal edges, on its face intended to come into contact with the skin, adherent elements to contribute to holding the sleeve on the member.

10. The orthosis according to claim 9, wherein the adherent elements are formed on straps, fixed to the proximal and distal edges of the sleeve, the straps being made of an elastic fabric that may be the same as the fabric of the sleeve.

11. The orthosis according to claim 10, wherein the strap of adherent elements fixed to the proximal edge of the sleeve comprises two straps fixed together and of different lengths to adapt to the shape of the member.

12. The orthosis according to claim 1, wherein the sleeve is less than 0.5 mm thick, and the plate is less than 1 mm thick.

13. The orthosis according to claim 1, wherein the plate is fixed to the sleeve along an inner edge of the annular part, by a proximal sector of the annular part and by a plate part including a distal sector of the annular part and the tab, and by assembly lines extending radially in relation to the plate and separating the proximal sector and the distal sector from two lateral sectors, outer side edges of the lateral sectors being left free.

14. The orthosis according to claim 13, wherein the two lateral sectors have an increased thickness with respect to the proximal sector and the distal sector of the plate.

* * * * *